United States Patent [19]

Williams

[11] Patent Number: Plant 7,596

[45] Date of Patent: Jul. 23, 1991

[54] MINIATURE ROSE PLANT/MINAWCO

[76] Inventor: Ernest D. Williams, 1510 Lebanon Ave., Dallas, Tex. 75208

[21] Appl. No.: 516,699

[22] Filed: Apr. 27, 1990

[51] Int. Cl.[5] ..... A01H 5/00

[52] U.S. Cl. ..... Plt./7

[58] Field of Search ..... Plt. 7–9

*Primary Examiner*—James R. Feyrer

[57] ABSTRACT

The subject of the present disclosure is a new and distinct variety of miniature rose plant characterized by warm rosy russet color of the double flowers and by the profusion of bloom.

1 Drawing Sheet

1

The present invention relates to a new and distinct variety of hardy, dwarf, bush type rose plant of the miniature class; the variety being primarily characterized—as to novelty—by the warm rosy russet coloration of the flowers which in general color effect are similar to Honey 'N Spice (miniature variety—not patented).

The variety is further characterized by:

The abundance of bloom, with flowers usually borne singly.

Fragrant.

A plant which is vigorous, of bushy, upright shape with semi-glossy to matt, small foliage, with pointed leaflets; the buds and flowers being similar in form and size to Amberglo (miniature—not patented), but averaging a few more petals.

The plant, which has a normal height of 12-14 inches or more, can easily be maintained at lesser height by occasional trimming.

A plant which grows and blooms satisfactorily outdoors; is good for growing in pots; and provides excellent garden decoration as well as cut flowers.

The present variety of miniature rose was originated by me at my nursery located at Dallas, Tex., under conditions of careful control and observation, as a cross between an unnamed seedling (a floribunda—not patented) as the seed parent and Yellow Jewel (miniature—U.S. Plant Pat. No. 3,627 expired) as the pollen parent.

Subsequent to origination of the variety I successfully reproduced it, at my nursery located as aforesaid, by cuttings; the reproductions having run true in all respects.

The color photograph illustrates the variety, including the foliage, bud and flowers.

Referring now specifically to the new and distinct variety of miniature rose plant, the following is a detailed description thereof in outline; all major color plate identifications being by reference to the R.H.S. Colour Chart, except where common terms of color definition are employed.

Type: Hardy; dwarf; bushy; upright; seedling; outdoors; cut flowers; garden decoration; potted plant.

Class: Miniature.

*Variety identification.*—Minawco.

*Commercial synonym.*—Suntan beauty.

Flowers borne: Usually singly on slender wirey stems.

Quantity of bloom: Abundant.

Bud:

2

*Peduncle.*—Medium to long length; slender but sturdy; erect; medium green, sometimes tinted bronze (outdoors);

*Hairs.*—few.

*Before calyx breaks; size.*—small. Form short; pointed with several foliaceous apendages and few or no tiny hairs on surface of bud; with foliaceous parts extending beyond the tip of the bud equal to one-half or less of its length.

*Color.*—Medium green, occasionally tinted with bronze (outdoors).

*As calyx breaks, color.*—Warm russet.

*Opening.*—Opens well in all weather.

Bloom:

*Size when fully open.*—Small, averaging about 35–40 mm (1½").

*Petalage double.*—Averaging about 40 petals, arranged regularly plus sometimes several small petaloids.

*Form.*—High centered, with petals reflexing loosely outward and later at maturity, rolled loosely outward and downward. Open flowers usually show stamens.

Petals: Fairly thick; satiny on inside and on outside surface.

*Shape.*—Outside petals, broad lanceolate — almost round; Intermediate — broad lanceolate with rounded top; Inside — lanceolate with slightly pointed tip.

Color: Newly opened flower from a plant grown outdoors (October 1988), Dallas, Tex.

*Outside petal.*—Outside surface — near and between Greyed Orange 175 B and C with an area of near white at base. The light areas of the petal edges are due to the intense October sunlight under which this illustration was taken. Cool weather highlights near Greyed Red 179 A and Greyed Red 178 A and B. Inside surface — Greyed Orange 172 A and B.

*Intermediate petal.*—Outside surface — similar to outside petal. Inside surface — similar to outside petal.

*Inner petal.*—Outside surface — same as intermediate petal; Inside surface — same as intermediate petal. Mature flowers are often tinted pinkish as they age. General color effect; newly opened flowers warm rosy russet. Three days open — color similar to newly opened flowers but less brilliant. Behavior — opens well in all weather. Color may become pinkish as flowers age.

Flower longevity (October 1988) — plant in pot 6–8 days or longer. Cut flowers at living room temperature 4–5 days or longer.

Reproductive organs:

*Stamens.*—About normal.

*Filaments.*—Varying length, yellowish.

*Anthers.*—Well formed; yellow.

*Pollen.*—Above average amount.

*Pistils.*—Average number.

*Styles.*—Uneven; medium to short length; bunched; Color — yellow.

*Ovaries.*—All enclosed in calyx.

*Hips.*—Few.

*Sepals.*—Permanent; spear shaped; recurved downward.

*Seed.*—Few.

Foliage:

*Leaves.*—Compound of five (sometimes three or seven) leaflets; fairly small; leathery; semi-glossy to matt.

*Leaflets.*—Shape: broad; nearly oval, apex acute; base rounded or rounded acute. Margin serrate. Color: medium to dark green; new growth — normal (medium) green. Rachis: medium strength; upper side may have a few tiny short prickles or hairs, grooved; underside sparsely thorny with few or no tiny prickles. Stipules: medium long; narrow points which turn out usually at about 45 degrees.

Growth:

*Habit.*—Dwarf; bushy; upright; much branched.

*Growth.*—Free vigorous; internodes short.

*Canes.*—Medium; slender; sturdy.

*Main stems.*—Color: medium green.

*Thorns.*—Few; slender short hooked downward, small base; color; light tan. Prickles — none. Hairs — none.

*Branches.*—Color: medium green. Thorns: few; short length; slender; nearly straight, inclined downward. Small oval base. Prickles: none. Hairs: none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, upright, much branched habit, substantially as illustrated and described, characterized by buds and flowers of a warm rosy russet color, being of a shade generally near and between Greyed Orange 175 A and B, the bud and flower resembling the variety Amberglo (not patented) in form and size but having more petals; and further characterized by a plant of vigorous and compact growth habit, easy to propagate from cuttings, with an abundance of flowers borne usually one to the stem.

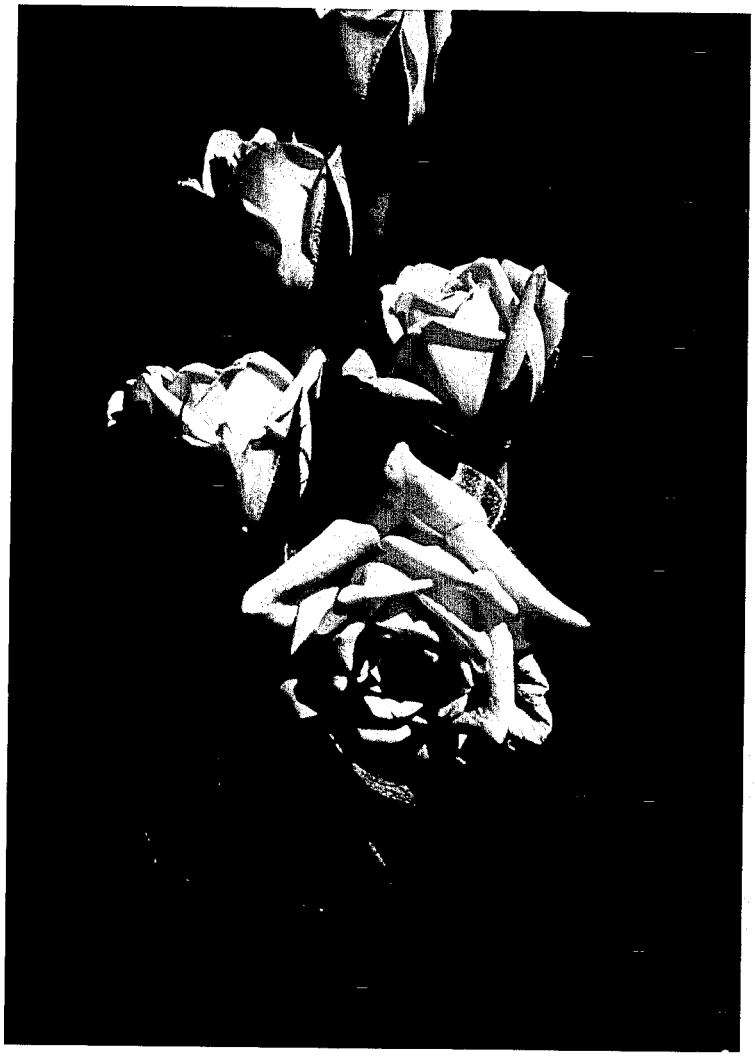

* * * * *